United States Patent [19]

Page

[11] Patent Number: 4,870,108

[45] Date of Patent: Sep. 26, 1989

[54] LIQUID ANTISEPTIC COMPOSITION

[76] Inventor: Leslie A. Page, 1723 Cypress Pt Glen, Escondido, Calif. 92026

[21] Appl. No.: 246,795

[22] Filed: Sep. 20, 1988

[51] Int. Cl.$^4$ ............................................. A61K 31/14
[52] U.S. Cl. ................................................... 514/642
[58] Field of Search ....................................... 514/642

[56] References Cited

U.S. PATENT DOCUMENTS 3,993,777  11/1976  Caughman et al. .................. 514/642

OTHER PUBLICATIONS

Lacey R. W. Chem. Abst: 9186x, vol. 69 (1968).
Remington's Practice of Pharmacy (1956).

*Primary Examiner*—Douglas W. Robinson
*Assistant Examiner*—Zohreh A. Fay

[57] ABSTRACT

A liquid antiseptic composition containing ethanol, acetone, a quaternary ammonium comound, glycerine, and water which is rapidly germicidal, non-staining, and non-irritating to the human skin is disclosed.

1 Claim, No Drawings

LIQUID ANTISEPTIC COMPOSITION

REFERENCES CITED

| INVENTOR |
| --- |
| Leslie A. Page |
| 1723 Cypress Pt Glen |
| Escondido, CA 92026 |
| REFERENCES CITED |
| U.S. Pat. Nos. |

| | | | |
| --- | --- | --- | --- |
| 3,443,141 | 1/1971 | Katsumi et al. | 252/106 |
| 3,594,468 | 7/1971 | Saurino et al. | 424/25 |
| 3,855,140 | 12/1974 | Billany et al. | 252/106 |
| 3,932,655 | 1/1976 | Conn | 424/317 |
| 3,960,745 | 6/1976 | Billany et al. | 252/106 |
| 3,965,026 | 6/1976 | Lancz | 252/106 |
| 4,247,424 | 1/1981 | Kuzel et al. | 252/153 |
| 4,464,293 | 8/1984 | Dobrin | 252/547 |
| 4,576,719 | 3/1986 | Paszek et al. | 252/106 |

OTHER PUBLICATIONS

"Alcohols", Chapter 10 by H. E. Morton, and "Surgical Antiseptics", Chapter 26 by W. A. Altemeier, in Disinfection, Sterilization, and Preservation, 3d Edition, by S. S. Block. Published by Lea Febiger, Philadelphia, 1983. pp 225–293 and 493–504.

"Antiseptics and Disinfectants", Chapter 41 by S. C. Harvey in Pharmaceutical Basis for Therapeutics, 7th Edition, by S. G. Gilman and L. S. Goodman, Published by Macmillan, New York, pp. 964–987.

"Disinfectant Activity Against Bacteria and Viruses: A Hospital Guide" by H. N. Prince, in Particulate and Microbial Control: Mar-Apr., 1983. Canon Communications.

BACKGROUND OF THE INVENTION

1. Field of the Invention

The present invention pertains to liquid compositions used as antiseptics by health care professionals or others to prevent transmission of potentially pathogenic microorganisms via the hands or skin from the professional to the patient and vice versa. More particularly, the present invention describes a novel formulation for a rapid-acting skin antiseptic that provides exceptional antimicrobial efficacy, cosmetic satisfaction, and economy of use-time because it eliminates the handwashing and toweling associated with the use of antiseptic soaps and scrubs.

2. Prior Art

The patents and specific scientific articles cited above plus a multitude of other references in the world literature describe numerous antimicrobial substances and various disinfectant compositions that have been recommended for use in the health care environment. The "other publications" referred to above describe the relative merits of various germicidal substances such as quaternary ammonium compounds, alcohols, ketones, chlorhexidines, iodophors, hexachloraphenes, propriolactines, and glycols. Published research on these substances has established the general ranges of concentrations of each substance that exerts the maximal germicidal activity relative to the class of microorganisms being challenged.

Five of the above referenced patentees incorporated a cationic detergent germicide, preferentially alkyl dimethyl benzyl ammonium chloride or variants thereof, in their disinfectant compositions along with non-anionic or amphoteric detergent stabilizers, alcohols, or scents to develop novel surface-disinfectant cleaners (Lancz, #3,965,026; Dobrin, #4,464,293), a surgical skin scrub concentrate (Conn, #3,932,655), or laundry detergents (Katsumi et al, #3,553,141; Paszek et al., (#4,576,729). In devising another antibacterial skin scrub, the sixth patentee (Bellany et al., #3,855,140 and 3,960,745) ruled out adding a cationic detergent germicide to this composition because of chemical antagonism between the detergent and their composition's major germicidal component, chlorhexidine.

The present invention differs from prior art in that my composition is comprised of compatible germicides of high volatility, which assure rapid germicidal action, and a germicide of relatively low volatility to assure residual antimicrobial activity/plus an emollient to protect the skin against dryness. The product is a skin antiseptic with the following general characteristics: (a) effective germicidal action in 30 seconds or less, (b) a high degree of germicidal activity against a broad spectrum of microorganisms, (c) non-staining, (d) non-irritating to the skin after repeated use, (d) residual antimicrobial activity after repeated use.

SUMMARY OF THE INVENTION

The invention is a liquid composition comprised of an aqueous mixture of two volatile germicides and one germicide of relatively low volatility and an emollient which when applied to the human skin as an antiseptic is rapid-acting against a broad spectrum of microorganisms, is non-staining, is non-irritating to the skin after repeated use, and leaves a residual antimicrobial activity on the skin after repeated use. The volatile germicides are ethanol and acetone, and the germicide of low volatility is alkyl dimethyl benzyl ammonium chloride, and the emollient is glycerine.

DETAILED DESCRIPTION OF PREFERRED EMBODIMENTS

The present invention is a liquid composition especially formulated to provide the health care professional with a skin antiseptic that assures rapid, effective, non-staining, non-irritating disinfection of their hands or other skin surfaces without time-consuming water-mediated washing and toweling. Such an antiseptic is of use as hand disinfectant prior to and after patient examinations where barrier protection such as that offered by rubber gloves is not needed or desired. Where gloves are required, the antiseptic may be used on the hands as a pre-gloving disinfectant to prevent the multiplication of microorganisms on the moist skin inside the rubber glove, thereby avoiding additional skin irritation. The antiseptic may also be used as a skin disinfectant for patients scheduled for venapuncture or surgery.

The present invention accomplishes the above objective with a liquid composition comprised of two volatile germicides that exert rapid, effective antimicrobial activity, a relatively non-volatile germicide the leaves a residual antimicrobial activity after repeated application of the composition, and an emollient that counteracts the dehydrating effects caused by the volatile germicides. An example of the ingredients and their concentrations of such a composition is as follows: ethanol, 64–70 wt %, acetone 5–6 wt %, alkyl dimethyl benzyl ammonium chloride, 0.06–0.10 wt %, glycerine 2.0–3.0 wt %. Deionized water brings the composition up to 100%.

Examples of sources of these ingredients are as follows: an ethanol-acetone-water mixture consisting of ethanol 85.73 wt %, acetone 7.24 wt %, and water 7.03 wt % can be purchased from the National Distillers and Chemical Corp. under permit from the U.S. Bureau of Alcohol, Tobacco and Firearms which classifies the mixture as Specially Denatured Alcohol 23A. Alkyl dimethyl benzyl ammonium chloride is available in a 10% aqueous solution from Sterling Drug Co. under the brand name Roccal II. Glycerine, USP, in 99.99% purity is available from any pharmacy or drug store.

EXAMPLES

The following examples further define the composition and manner of preparation, and describe the characteristics of the products.

EXAMPLE I

In the simplest manner of preparation, 1 gallon of glycerine and 0.25 gallon of Roccal II is added to 11 gallons of de-ionized water in a suitable vessel and stirred for 5 min. This mixture is then added to 46 gallons of SDA 23A ethanolacetone-water mixture at 20 C. in a container suitable for stirring flammable liquids and the new mixture is stirred for 5–10 minutes. Adequate stirring is assured if samples of the product taken at various levels in the container all have the same "proof" measurement as determined by use of a proof hydrometer. The percent by weight of each ingredient in the final product is presented below.

were challenged with test carriers heavily seeded with *Salmonella cholerasuis, Staphylococcus aureus,* or *Pseudomonas aeruginosa,* 60 carriers/culture/sample of product. Of the total of 540 seeded carriers treated with the antiseptic product, none demonstrated subsequent growth of any microorganisms after appropriate incubation. The second laboratory had the same results using 10 carriers/product sample against the same three species of bacteria as well as the fungus Tricophyton mentaqroohvtes A third laboratory demonstrated 99.99% reductions in the numbers of *Mycobacteria bovis* in a milieu of blood or poliovirus in a milieu of blood surviving 30 second contact with the above product. A fourth laboratory made counts of the normal bacteria on each fingertip of each of 20 human volunteers before and after a 30 second application of the above antiseptic product, no surviving bacteria were detected on any fingertip of 12 of the volunteers. The remaining volunteers had an average reduction of 98% in the bacterial count after antiseptic application. Furthermore, none of the above volunteers nor 25 other persons using the product for 3 months or more on a regular daily basis reported any skin irritation caused by the product. Also in clinical trials, professionals who substituted use of this product for handwashing with disinfectant soaps reported rapid improvement in the condition of fingertip skin that had shown drying and cracking due to repeated daily handwashing between patient examinations.

The foregoing tests are significant in that they indi-

| Ingredient | Volume (gallons) | Equivalent wt in lbs | Final wt % in composition |
|---|---|---|---|
| SDA 23A ethanol-acetone-water mixture consisting of: | 46 | | |
| ethanol 85.73 wt % | | 267.69 | 64.24 |
| acetone 7.24 wt % | | 22.50 | 5.40 |
| water 7.03 wt % | | 21.95 | 5.27 |
| Roccal II, aqueous 10% solution of alkyl dimethyl benzyl ammonium chloride | 0.25 | 2.80 | 0.67* |
| Glycerine, USP | 1.0 | 10.45 | 2.51 |
| Deionized water | 11.0 | 91.3 | 21.91 |
| | | | 100.00 |

*Because Roccal 11 is a 10% solution of alkyl dimethyl benzyl ammonium chloride, the final concentration of this ingredient in the composition is 0.067 wt %.

The product of the above example is a liquid antiseptic composition in accordance with the present invention.

To validate the antimicrobial efficacy of the above product, samples of the product were tested by two commercial laboratories approved by the U.S. Environmental Protection Agency to evaluate disinfectants. The laboratories followed testing protocols recommended in Official Methods of Analysis of the AOAC, 14th Ed., 1984, which meet EPA DIS/TSS 1 & 2 requirements. Each of the three samples of the product cate that the product of Example I has rapid, effective antimicrobial activity as well as satisfactory cosmetic action on the skin.

Example II

The concentrations of the active ingredients are increased over those in Example I by the expedient of mixing less de-ionized water to the glycerolbenzalkonium mixture with the resulting changes in weight percents shown in the table below.

| Ingredient | Volume (gallons) | Equivalent wt in lbs | Final wt % in Composition |
|---|---|---|---|
| SDA 23A ethanol-acetone mixture consisting of: | 46 | | |
| ethanol 85.73 wt % | | 267.69 | 68.33 |
| acetone 7.24 wt % | | 22.50 | 5.75 |
| water 7.03 wt % | | 21.95 | 5.60 |
| Roccal II (10% benzalkonium-Cl) | 2.8 | 2.80 | 0.71* |
| Glycerol | 1.0 | 10.45 | 2.66 |
| De-ionized water | 8.0 | 66.4 | 16.95 |

| Ingredient | Volume (gallons) | Equivalent wt in lbs | Final wt % in Composition |
|---|---|---|---|
| | | | 100.00 |

*Because Roccal II is a 10% solution of the active ingredient, the actual percentage by weight of the this ingredient in composition is 0.071 wt %.

The antimicrobial efficacy of the product of example 2 was compared with the product of example 1 by a bacterial growth-inhibition zone method where the surfaces of sterile 5%-ovine-blood tryptose-soy agar bacteriological plates were heavily seeded with cultures of Staphylococcus epidermidis, a human skin isolant, and 0.01 ml samples of each product were pipetted onto sterile 4 mm pads placed in various sectors of the seeded surfaces. The plates were incubated at 37 C. for 30 hours, and the diameters of circular zones of inhibition of bacterial growth surrounding each pad were measured. Averages of the diameters of zone of inhibition of 20 samples of each product indicated that the product of Example 11 had 5% increase in antimicrobial activity against the test organism. However, it was observed that the second product took longer to dry on the skin of users. Therefore, the product of Example I was adjudged more satisfactory for general use.

Although a particular embodiment of the invention has been described and illustrated herein, it is recognized that modifications and variations may readily occur to those skilled in the art and consequently, it is intended that the claims be interpreted to cover such modifications and equivalents.

I claim:

1. A liquid composition for use in the health care environment as a rapid-acting skin antiseptic consisting essentially of:
   a. from about 64 to 70 wt % of a primary germicide with high volatility and rapid-acting antimicrobial activity consisting essentially of ethanol,
   b. from about 5.0 to 6.0 wt % of a secondary germicide with high volatility consisting essentially of acetone,
   c. from about 0.06 to 0.10 wt % of a germicide with relatively low volatility consisting essentially of alkyl ($C_{14}$-50%, $C_{12}$-40%, $C_{16}$-10%) dimethyl benzyl ammonium chloride,
   d. from about 2.0 to 3.0 wt % of an emollient consisting essentially of glycerine,
   e. with the remaining percentage made up of de-ionized water.

* * * * *